United States Patent
Hultander et al.

(10) Patent No.: US 12,336,896 B2
(45) Date of Patent: Jun. 24, 2025

(54) ABSORBENT ARTICLE

(71) Applicant: Essity Hygiene and Health Aktiebolag, Gothenburg (SE)

(72) Inventors: Björn Hultander, Gothenburg (SE); Helena Corneliusson, Gothenburg (SE)

(73) Assignee: Essity Hygiene and Health Aktiebolag, Gothenburg (SE)

( * ) Notice: Subject to any disclaimer, the term of this patent is extended or adjusted under 35 U.S.C. 154(b) by 450 days.

(21) Appl. No.: 17/913,247

(22) PCT Filed: Apr. 20, 2020

(86) PCT No.: PCT/SE2020/050398
§ 371 (c)(1),
(2) Date: Sep. 21, 2022

(87) PCT Pub. No.: WO2021/215972
PCT Pub. Date: Oct. 28, 2021

(65) Prior Publication Data
US 2023/0114320 A1      Apr. 13, 2023

(51) Int. Cl.
*A61F 13/15* (2006.01)
*A61F 13/494* (2006.01)
(Continued)

(52) U.S. Cl.
CPC ...... *A61F 13/535* (2013.01); *A61F 13/49446* (2013.01); *A61F 13/515* (2013.01);
(Continued)

(58) Field of Classification Search
CPC .............. A61F 13/535; A61F 13/49446; A61F 13/515; A61F 2013/15869; A61F 2013/15878; A61F 2013/530481
(Continued)

(56) References Cited

U.S. PATENT DOCUMENTS 10,736,794 B2    8/2020  Roe et al.
10,849,799 B2   12/2020  Nishikawa et al.
(Continued)

FOREIGN PATENT DOCUMENTS

EP    3318237 A1    5/2018
EP    3403626 A1   11/2018
(Continued)

OTHER PUBLICATIONS

Extended European Search Report issued in European Patent Application No. 20932542.2-1102, dated Dec. 20, 1 2023 (7 pages).
(Continued)

*Primary Examiner* — Jacqueline F Stephens
(74) *Attorney, Agent, or Firm* — Buchanan Ingersoll & Rooney PC (57) ABSTRACT

An absorbent article comprising an absorbent core comprising absorbent material. The absorbent core is sandwiched between a liquid-permeable upper core cover layer and a lower core cover layer. The absorbent core has one or more elongated areas arranged therein, each elongated area being an absorbent material free area having a length as measured along the elongated area and a width. The upper core cover layer and the lower core cover layer in each of the one or more elongated absorbent material free areas are attached to each other within at least 2 attachment zones and at most 12 attachment zones, the attachment zones being spaced-apart in the longitudinal direction (Y) within each of the one or more absorbent material free areas.

21 Claims, 4 Drawing Sheets

(51) Int. Cl.
    *A61F 13/515*    (2006.01)
    *A61F 13/535*    (2006.01)
    *A61F 13/53*     (2006.01)
(52) U.S. Cl.
    CPC .............. *A61F 2013/15869* (2013.01); *A61F 2013/15878* (2013.01); *A61F 2013/530481* (2013.01)
(58) Field of Classification Search
    USPC ........................................ 604/378, 379, 380
    See application file for complete search history.

(56) References Cited

U.S. PATENT DOCUMENTS

| | | | |
|---|---|---|---|
| 2015/0173968 A1 | 6/2015 | Joseph | |
| 2016/0206483 A1 | 7/2016 | Nishikawa et al. | |
| 2017/0135871 A1* | 5/2017 | Kamphus | A61F 13/5323 |
| 2017/0312146 A1 | 11/2017 | Bianchi et al. | |
| 2019/0117476 A1 | 4/2019 | Bianchi | |
| 2019/0117477 A1 | 4/2019 | Bianchi | |
| 2020/0078229 A1 | 3/2020 | Van Ingelgem et al. | |
| 2020/0276059 A1 | 9/2020 | Smet et al. | |
| 2020/0337909 A1 | 10/2020 | Sillerström et al. | |

FOREIGN PATENT DOCUMENTS

| | | |
|---|---|---|
| EP | 3403627 A1 | 11/2018 |
| EP | 3403628 A1 | 11/2018 |
| EP | 3473222 A1 | 4/2019 |
| EP | 3473223 A1 | 4/2019 |
| EP | 3473224 A1 | 4/2019 |
| EP | 3562454 A1 | 11/2019 |
| EP | 3752114 A1 | 12/2020 |
| JP | 2016112404 A | 6/2016 |
| WO | 2016114946 A1 | 7/2016 |
| WO | 2016191260 A1 | 12/2016 |
| WO | 2017087155 A1 | 5/2017 |
| WO | 2017189151 A1 | 11/2017 |
| WO | 2018122234 A1 | 7/2018 |
| WO | 2019048397 A1 | 3/2019 |
| WO | 2019083767 A1 | 5/2019 |
| WO | 2019125229 A1 | 6/2019 |
| WO | 2019125231 A1 | 6/2019 |
| WO | 2019125232 A1 | 6/2019 |
| WO | 2019158226 A1 | 8/2019 |

OTHER PUBLICATIONS

Office Action (Communication) issued on Jul. 9, 2024, by the European Patent Office in corresponding European Patent Application No. 20 932 542.2. (4 pages).

International Preliminary Report on Patentability and Written Opinion of the International Searching Authority (Forms PCT/IB/326, PCT/IB/373 and PCT/ISA/237) issued on Nov. 3, 2022, by the International Bureau of WIPO, in corresponding International Application No. PCT/SE2020/050398. (9 pages).

International Search Report (PCT/ISA/210) and Written Opinion (PCT/ISA/237) mailed on Dec. 21, 2020, by the Swedish Patent and Registration Office as the International Searching Authority for International Application No. PCT/SE2020/050398. (14 pages).

Office Action issued on Apr. 9, 2025, by the Intellectual Property Corporation of Malaysia in corresponding Malaysian Patent Application No. PI20222005258, English Translation of the Office Action. (4 pages).

\* cited by examiner

ABSORBENT ARTICLE

TECHNICAL FIELD

The disclosure pertains to an absorbent article comprising an absorbent core, the absorbent core comprising absorbent material and being sandwiched between an upper liquid-permeable cover layer and a lower cover layer.

BACKGROUND

In disposable absorbent articles, such as baby diapers and other articles for absorption of body fluids such as pant-type absorbent garments, incontinence protectors and sanitary napkins, there is a conflict between the requirement of sufficient absorption capacity and leakage security on the one hand and wearer comfort and discretion on the other hand. Accordingly, there is a demand for highly efficient absorbent articles which are flexible and conform well to the body of a wearer so that the wearer does not feel restricted or uncomfortable when wearing the absorbent article. In order to provide sufficient absorption capacity while offering thin absorbent articles, a large proportion of the absorbent material may be what is commonly known as superabsorbent material. Superabsorbent materials are polymeric materials usually incorporated into the absorbent articles in the form of fibres, particles or granules. Superabsorbent materials can absorb many times their own weight of fluid upon swelling and formation of a hydrogel. Absorbent articles which contain a large amount of superabsorbent material have been found to lose their initial flexibility and wearer comfort as they absorb liquid and swell. In particular, high-impact areas of an absorbent article, such as the crotch portion of a diaper which contains a large amount of absorbent material distributed over a relatively small area may grow thick and stiff as the article absorbs liquid. Moreover, it is a concern in the area of disposable absorbent articles that the available absorption capacity of the absorbent material may be utilized as fully as possible, in order to keep material consumption at a minimum when producing the absorbent articles.

A further disadvantage which may arise during wearing of the absorbent article is that the crotch portion may sag and hang down between the legs of the wearer. Sagging of the absorbent article may cause discomfort and may negatively affect the fit and proper function of the absorbent article. Sagging of a baby diaper may further lead to the baby being hampered when trying to move while wearing the sagging diaper.

To this end, it has been suggested in WO2019/125231 A1 to form two longitudinally extending channel sealings in an absorbent core in an absorbent article. The absorbent core is enclosed within a core cover and the channel sealings join an upper side of the core cover with a lower side of the core cover and are arranged such that they divide the absorbent core into a centre segment and two side segments. When the absorbent material in the absorbent core absorbs body fluids and swells, the core cover acts as a swelling restriction means limiting the swelling room for the absorption material in the different segments. Thereby, the expanding absorption material exerts outward pressure on the core cover resulting in an increase in stiffness of the absorbent core in the crotch portion of the absorbent article. Particularly high stiffness may thereby be achieved in the centre segment between the two channel sealings.

SUMMARY

The present disclosure is based on the insight that an absorbent article having improved fit, body conformance and wearer comfort as well as good functionality regarding absorbency and leakage security, may be achieved at least in part by the features of claim 1. Variations of the disclosure are set out in the dependent claims and in the following description.

The absorbent articles referred to herein may be wearable disposable absorbent articles, for example in the form of open diapers, pant diapers, belted diapers, incontinence garments, feminine hygiene garments and the like, as well as disposable absorbent inserts, e.g. incontinence shields or sanitary napkins, which are worn inside a support garment, such as a support pant or ordinary underwear. The articles are used to absorb, distribute and store various types of body exudates while providing a high level of comfort and a sense of dryness to the wearer during wearing.

An absorbent article as disclosed herein comprises an absorbent core, the absorbent core comprising absorbent material. The absorbent core is sandwiched between a liquid-permeable upper core cover layer and a lower core cover layer. The article has a longitudinal direction and a transverse direction perpendicular to the longitudinal direction. The absorbent core has a first side edge and a second side edge, the first side edge and the second side edge of the absorbent core each extending in the longitudinal direction. The upper core cover layer and the lower core cover layer are connected along the side edges of the absorbent core. The absorbent core has one or more elongated areas arranged therein, each elongated area being an absorbent material free area and having a main extension in the longitudinal direction with a length as measured along the elongated area and a width in the transverse direction, wherein the upper core cover layer and the lower core cover layer in each of the one or more elongated absorbent material free areas are attached to each other within at least 2 attachment zones and at most 12 attachment zones, the attachment zones being spaced-apart in the longitudinal direction within each of the one or more absorbent material free areas.

By an absorbent material free area as used herein, is implied an area which is at least substantially free from absorbent material, such that the upper and lower core cover layers can be bonded together in the absorbent material free area and such that the absorbent material free area between the attachment zones in the absorbent material free area may provide expansion room for the absorbent material on either side of the absorbent material free area. Hence, the absorbent material free areas as disclosed herein, may contain small amounts of absorbent material, e.g. as a result of imperfections in a production process or due to dislocation of fibres or particles from the adjacent absorbent material during packaging and handling of the absorbent article.

The attachments between the upper core cover layer and the lower core cover layer in the one or more absorbent material free areas stabilize the absorbent core and prevent absorbent material from moving freely and becoming redistributed in an uncontrolled and undesired manner between the upper core cover layer and the lower core cover layer. During use of the absorbent article, the absorbent core will absorb body fluid and swell. The attachment zones in which the upper core cover layer and the lower core cover layer are connected with each other constitute restriction means which limit swelling in a thickness direction of the absorbent article by prohibiting the upper core cover layer and the lower core cover layer from freely moving away from each other. The combination of absorbent material free areas and spaced-apart attachment zones arranged in the absorbent material free areas provides an absorbent core in which swelling of the absorbent material may be controlled by allowing the absorbent material on either side of an absorbent material free area to expand into the absorbent material free area. The absorbent material will expand in the transverse direction of the absorbent article between the attachment zones and into the expansion volume offered by the parts of the absorbent material free area which are located between the attachment zones.

Further the absorbent core may be somewhat narrower than the core cover, giving the absorbent core room to expand in the transverse direction towards the side edges of the core cover. Expansion room may also be provided in the longitudinal direction, either by providing an open-ended core cover or by the absorbent core being shorter than a core cover having closed ends.

When referring to dimensions of the components in the absorbent articles and the absorbent cores as disclosed herein the dimensions are determined when the absorbent articles and the absorbent cores are in a dry state, i.e. before having absorbed any liquid, unless explicitly stated that the dimensions are determined in a wet state, after absorption of liquid.

The absorbent articles as disclosed herein have been found to counteract sagging by the provision of the core stabilizing attachment zones as well as by the provision of an expansion volume promoting lateral expansion of the absorbent material in the absorbent core as the absorbent material absorbs fluid and swells. The absorbent cores and thereby the absorbent articles as disclosed herein retain much of their flexibility and body conformability even after having absorbed body fluid as the absorbent material may be redistributed in the transverse direction of the absorbent article while swelling is restricted in the thickness direction of the absorbent article. Uncontrolled, swelling in the thickness direction resulting in unsightly bulging and sagging of the article is thereby reduced. Furthermore, stiffened portions which may potentially be perceived as being less comfortable are also avoided by the absorbent material being able to swell and expand in the transverse direction of the absorbent article.

The absorbent core may be a component of an absorbent assembly comprising further components or layers, such as one or more of an acquisition layer, a liquid transfer layer, a liquid distribution layer, a further absorbent core, etc. Alternatively, the absorbent core may be the only absorbent component of the absorbent article.

In the absorbent article as disclosed herein, both the upper core cover layer and the lower core cover layer may be liquid-permeable cover layers together forming a liquid permeable core cover. The upper core cover layer and optionally also the lower core cover layer may be a hydrophilic layer. Hydrophilicity may be accomplished by incorporating inherently hydrophilic fibers in the core cover layer, such as cellulose fibers or regenerated cellulose fibers, e.g. wood pulp fibers, cotton, flax, hemp, viscose, etc. as known in the art. Hydrophilicity may also be accomplished by treating inherently hydrophobic materials such as polymeric films and fibers, e.g, polyolefins such as polyethylene and polypropylene, polyesters, etc. to render them hydrophilic and wettable.

The lower core cover layer may be liquid impermeable and/or hydrophobic. An absorbent core being enclosed in a liquid permeable core cover may be a component in a wearable absorbent article such as an open diaper, a pant diaper, a belted diaper, an incontinence garment, a feminine hygiene garment or the like. Such wearable absorbent articles generally comprise one or more further components such as a further absorbent core, an acquisition layer, a transfer layer, a topsheet, a backsheet, etc.

Thus, the upper core cover layer and the lower core cover layer may together form a core cover. The upper core cover layer and the lower core cover layer may be formed from a single continuous material layer or from two separate material layers.

As disclosed herein, the absorbent article may in addition to the upper core cover layer and the lower core cover layer comprise a liquid permeable topsheet and a liquid barrier layer, the absorbent core being arranged between the liquid permeable topsheet and the liquid barrier layer with the upper core cover layer facing the liquid permeable topsheet and the lower core cover layer facing the liquid barrier layer.

As disclosed herein, the core cover may be formed by a separate upper core cover layer and a separate lower core cover layer forming the lower side of the core cover, the upper and lower core cover layers together enclosing the absorbent component and being sealed together at least along the side edges of the absorbent core. Preferably, the upper and lower core cover layers are sealed together along the full periphery of the absorbent core.

When the core cover is formed from a single material layer, the single material layer may be wrapped around the absorbent core or may be formed as a tubular structure into which the absorbent component is inserted. The core cover is sealed at least in the longitudinal direction, which means that the ends of the core cover may be left open. Preferably, the core cover is sealed so that the absorbent core is completely enclosed inside the core cover. Furthermore, the core cover may be made from more than two material layers.

The basis weight of the core cover materials as used herein may be in the range of from 5 $g/m^2$ to 20 $g/m^2$. The core cover material may be made of thermoplastic polymer material, such as polyolefin, polyesters, polyamide and combinations thereof. The core cover material may be a nonwoven material, a perforated plastic film, a netting, etc. A nonwoven layer may be formed by any of a variety of different processes, as known in the art, such as spunbonding, airlaying, meltblowing or bonded carded web formation processes. The nonwoven layer may be made of co-formed lamina of nonwoven materials such as an SMS (spunbond/meltblown/spunbond) nonwoven material an SMMS nonwoven material (spunbond/meltblown/meltblown/spunbond) or an SS (spunbond/spunbond) nonwoven material. The thermoplastic polymer materials in the nonwoven layer may be polypropylene or bicomponent fibers of polypropylene and polyethylene, or of a combination of such materials.

The absorbent core may be constituted by one single absorbent component layer. Absorbent cores comprising two or more layers are also contemplated for the absorbent articles as disclosed herein.

The absorbent core may have a rectangular shape or any other suitable shape as known in the art such as hourglass shape, dogbone shape T-shape, H-shape, etc. A rectangular absorbent core may have the advantage of being easy to manufacture and enclose in a core cover.

In an absorbent article as disclosed herein, the upper core cover layer may be a liquid permeable topsheet and the lower core cover layer may be a liquid barrier layer, such as a liquid impermeable backsheet. In an absorbent article of this kind, the absorbent core is the only absorbent component of the absorbent article. The absorbent article may be an incontinence protector, a sanitary napkin, or the like.

The absorbent core may comprise super-absorbent material, such as from 30% by weight to 100% by weight of superabsorbent material, from 50% by weight to 90% by weight of superabsorbent material or from 60% by weight to 80% by weight of superabsorbent material. The absorbent core may comprise a mixture of absorbent cellulose fibers, such as cellulose pulp fibers and superabsorbent polymer material in the form of particles, granules, fibers, flakes, etc. The amount of cellulose pulp fibers in the absorbent core may make up the remaining part of the absorbent core. Accordingly, the amount of cellulose pulp fibers may be from 70% by weight to 0% of cellulose pulp fibers, or from 50% by weight to 10% by weight of cellulose pulp fibers or from 40% by weight to 20% of cellulose pulp fibers.

The total absorbent capacity per cubic centimeter of the absorbent core in a dry condition may be at least 15 g/cm$^3$, or at least 25 g/cm$^3$ or at least 35 g/cm$^3$.

Cellulose pulp fibers in the absorbent core may have a basis weight within the range of from 50 to 400 g/m$^2$ and the superabsorbent material may have a basis weight which is in the range of from 100 to 900 g/m$^2$.

The thickness of the absorbent core in a dry condition, measured with an applied pressure of 0.5 kPa, may be in the range of from 2.0 mm to 15.0 mm or from 2.5 mm to 10 mm or from 3.0 to 8.0 mm.

The attachment zones may be spaced apart in the longitudinal direction with a closest distance in the longitudinal direction between neighboring attachment zones of from 15 millimeters to 110 millimeters, or from 20 millimeters to 100 millimeters or from 30 millimeters to 80 millimeters. A typical spacing between the attachment zones may be in the range of from 35 millimeters to 50 millimeters. Such spacing has been found to provide a good balance between creating core stability and providing adequate expansion room.

The attachment zones may have a length/width ratio of 1/1 or a length/width ratio within the range of from 0.8/1 to 4/1, such as within the range of from 0.9/1 to 3/1, within the range of from 1/1 to 2/1 or within the range of from 1/1 to 1.5/1. The attachment zones each have a length, i.e, an extension in the length direction of the absorbent article which is considerably smaller than the length of the one or more absorbent material free areas. Each attachment zone may have a length being in the range of from 1.5% to 5% of the length of the absorbent material free area in which the attachment zone is arranged, such as from 2% to 4% of the absorbent material free area in which the attachment zone is arranged. Furthermore, the width of each attachment zone may be smaller than the width of the absorbent material free area, such that the width of each attachment zone is in the range of from 40% to 95% of the width of the absorbent material free area, such as from 50% to 90% of the width of the absorbent material free area, or from 60% to 85% of the width of the absorbent material free area.

The attachment zones may be of the permanent type. A permanent attachment is sufficiently strong to resist breaking up when the absorbent material absorbs liquid and expands.

The attachment areas may be formed by welding, such as heat welding or ultrasonic welding. Other attachment means may be used, such as adhesive bonding or needling.

Each attachment zone may consist of a single weld bond or of a cluster of 2 to 200 individual weld bonds, such as a cluster of 3 to 100 individual weld bonds, or a cluster of 4 to 50 individual weld bonds, or a cluster of 5 to 25 individual weld bonds. For incontinence applications such as baby diapers, a number of individual weld bonds in a cluster in the range of from 4 to 20 individual weld bonds has been found to work well.

The individual weld bonds may be point bonds each having a bond area in the order of 0.5 mm$^2$, or from 0.3 mm$^2$ to 4 mm$^2$. The individual point bonds may have any suitable shape, such as oval, circular, triangular, rectangular (including square), etc. The individual point bonds are closely spaced within the attachment zone with a centre to centre spacing in the order of from 0.8 mm to 6 mm, such as from 0.9 mm to 4 mm or from 1.0 mm to 3.0 mm. The individual point bonds may be arranged in the attachment zone in a staggered pattern or in any other suitable pattern.

The overall outline or shape of an attachment zone may be determined by the arrangement of individual point bonds within the attachment zone. The attachment zone may have a geometric shape such as a generally rectangular shape, a circular or oval shape, etc., or the point bonds may be arranged to give the attachment zone a more figurative shape, such as a heart shape, a star shape, etc.

The length of each of the one or more elongated absorbent material free areas may be in the range of from 50 mm to 500 mm, such as from 100 mm to 300 mm or from 150 mm to 200 mm and the width being in the range of from 3 mm to 30 mm, such as from 5 mm to 25 mm, such as from 7 mm to 20 mm, or from 10 mm to 15 mm. The dimensions of the one or more elongated absorbent free areas are generally adapted to the size of the absorbent article. Smaller articles, such as diapers for premature and newborn babies, sanitary napkins and incontinence protectors may have elongated absorbent material free areas having lengths and widths in the lower parts of the ranges, e.g. a length within the range of from 50 to 150 mm and a width of from 3 to 15 mm. Diapers for older children may have a length and a width in the intermediary ranges, e.g. a length within the range of from 100 mm to 215 mm and a width within the range of from 7 mm to 15 mm. Even larger articles, such as adult incontinence garments and inserts may have elongated absorbent material free areas having lengths and widths in the upper parts of the ranges, e.g. a length within the range of from 180 mm and a width within the range of from 10 to 30 mm. The width of the one or more absorbent material free areas will generally differ less between different types of articles and different article sizes than the length of the absorbent material free areas.

Each attachment zone may have a surface area in the range of from 3 mm$^2$ to 400 mm$^2$, or from 4 mm$^2$ to 200 mm$^2$, or from 5 mm$^2$ to 100 mm$^2$, or from 7 mm$^2$ to 20 mm$^2$.

The absorbent core may comprise more than one elongated absorbent material free area, such as 2 to 10 elongated absorbent material free areas, or 3 to 8 elongated absorbent material free areas. The absorbent core may comprise two elongated absorbent material free areas being symmetrically arranged on each side of a center line extending in the longitudinal direction of the absorbent article. The absorbent material free areas may be straight absorbent material free areas extending parallel with each other and with the longitudinally extending center line, or may deviate from a straight extension, e.g. by having a curved shape.

When the absorbent core is provided with two absorbent material free areas, the absorbent core may be divided into a central segment located between the absorbent material free areas and two side segments. The absorbent material free areas are consequently configured so that they separate three core segments from each other in the absorbent core.

The central segment is defined in the absorbent core between the two absorbent material free areas and the two side segments, are defined in the absorbent core laterally outside each absorbent material free area. More precisely, a first side segment is formed between one of the absorbent material free areas and a corresponding side edge of the absorbent core and a second side segment is formed between the other absorbent material free area and the corresponding side edge of the absorbent core. As set out herein, side seams may be arranged along the side edges of the absorbent core, the side seams being configured for joining the upper core cover layer to the lower core cover layer along the side edges of the absorbent core. Alternatively, one or both of the side edges of the absorbent core may be covered by a fold in a core cover material. Side seams may suitably be formed by means of ultrasonic welding or other relevant technologies as described herein with reference to the attachment zones in which the upper cover layer and the lower cover layer are joined in the absorbent material free areas.

The one or more absorbent material free areas as disclosed herein may be arranged only in a crotch portion of the absorbent core, i.e. within a portion of the absorbent core which is intended to be positioned in the crotch of a wearer when the absorbent article is being worn. The length of the crotch portion may then be defined as the length of the one or more absorbent material free areas.

The absorbent core may comprise two or more parts having different absorption capacity, each of the at least one or more elongated areas being arranged in the one or more parts having different absorption capacity, wherein the attachment zones in each of the one or more elongated areas are more closely spaced apart within a part of the absorbent core having lower absorption capacity than in a part of the absorbent core having higher absorption capacity.

Parts of the absorbent core which comprises high amounts of absorbent material, in particular such parts of the absorbent core which comprise high amounts of superabsorbent material needs more expansion room in order to reach its full absorption capacity. For this reason it may be beneficial to arrange the attachment zones with greater spacing within such parts than within parts of the absorbent core having less absorption capacity and less absorption material. In such parts of the absorbent core more closely spaced attachment zones may serve to stabilize the absorbent core and to immobilize the absorption material such that it stays in place and is not redistributed in an undesired way. Undesired redistribution of the absorbent material may cause the formation of lumps and cracks in the absorbent core, which may impair the performance of the core.

The absorbent core may comprise a forward part and a rear part. The forward part of the absorbent core is intended to be placed in the crotch of a wearer and to optionally also extend forward from the crotch when the article is being worn. The rearward part of the absorbent core is intended to extend rearward from the crotch of the wearer and to lie over the buttocks of the wearer, when the article is being used. It is normally expected that a major part of body fluid will be absorbed in the forward part of a diaper or an incontinence article, while the rear part of the absorbent article is expected to receive a lesser amount of body fluid. For this reason, the rear part of the absorbent core may be provided with less absorbent capacity, i.e. the absorbent material is applied with a lower basis weight in the rear part than in the forward part of the absorbent core and/or a smaller amount or no superabsorbent material is applied in the rear part of the absorbent core than in the forward part of the absorbent core.

In a low absorbency zone, e.g. in a low absorbency rear part of the absorbent core, the attachment zones may be spaced apart in the longitudinal direction with a closest distance in the longitudinal direction between neighboring attachment zones of from 30 mm to 110 mm or from 35 to 80 millimeters. In a high absorbency zone, e.g. in a high absorbency forward part of the absorbent core, the attachment zones may be spaced apart in the longitudinal direction with a closest distance in the longitudinal direction between neighboring attachment zones of from 15 mm to 70 mm or from 35 mm to 50 mm. The spacing in the low absorbency zone is selected to be greater than the spacing in the high absorbency zone.

The absorbent article may be a baby diaper. As used herein the term "baby diaper" refers to an open-type absorbent garment which is provided with fastener elements to allow the garment to be applied to the lower torso of a baby in the manner of a pair of under pants. However, the absorbent article as disclosed herein, may be any type of hygienic absorbent article for absorbing body fluids and feces from the nether regions of a user. Accordingly, the absorbent article may be a pull-up absorbent pant for children or adults or an absorbent insert which is applied inside a support garment such as an incontinence protector or a sanitary napkin. Absorbent articles which are fastened on a wearer's body by means of a belt or a girdle are also contemplated.

As disclosed herein, the absorbent article may be provided with components such as elastic barrier cuffs, elastic side panels, skin care agents, odour control material and other components which are commonly used in absorbent articles such as for example baby diapers or incontinence garments. Such additional components are well known in the art and are not described in further detail here.

The absorbent article as disclosed herein may be varied within the scope of the appended claims. For example, the materials and dimensions used for the different layers forming an absorbent article as disclosed herein may be varied, as indicated above. The absorbent article may further include any useful component or feature as known in the art such as fluid acquisition and distribution components, leg elastics, standing gathers, crotch and waist elastics, side panels, fastening systems, wetness indicators, skin care agents, disposal means, etc., as known in the art and depending of the type of absorbent article intended.

BRIEF DESCRIPTION OF THE DRAWINGS

The absorbent articles as disclosed herein will be further explained hereinafter with reference to the appended drawings wherein.

DETAILED DESCRIPTION

Different aspects of the present disclosure will be described more fully hereinafter with reference to the enclosed drawings. The embodiments disclosed herein can, however, be realized in many different forms and should not be construed as being limited to the aspects set forth herein. In particular, it is to be understood that although the absorbent article shown in the Figures is a baby diaper, the expansion controlling absorbent material free areas with the attachment zones created between an upper core cover layer and a lower core cover layer are applicable to any disposable absorbent article as disclosed herein.

It is to be understood that the drawings are schematic and that individual components, such as layers of material are not necessarily drawn to scale.

Figure 1:
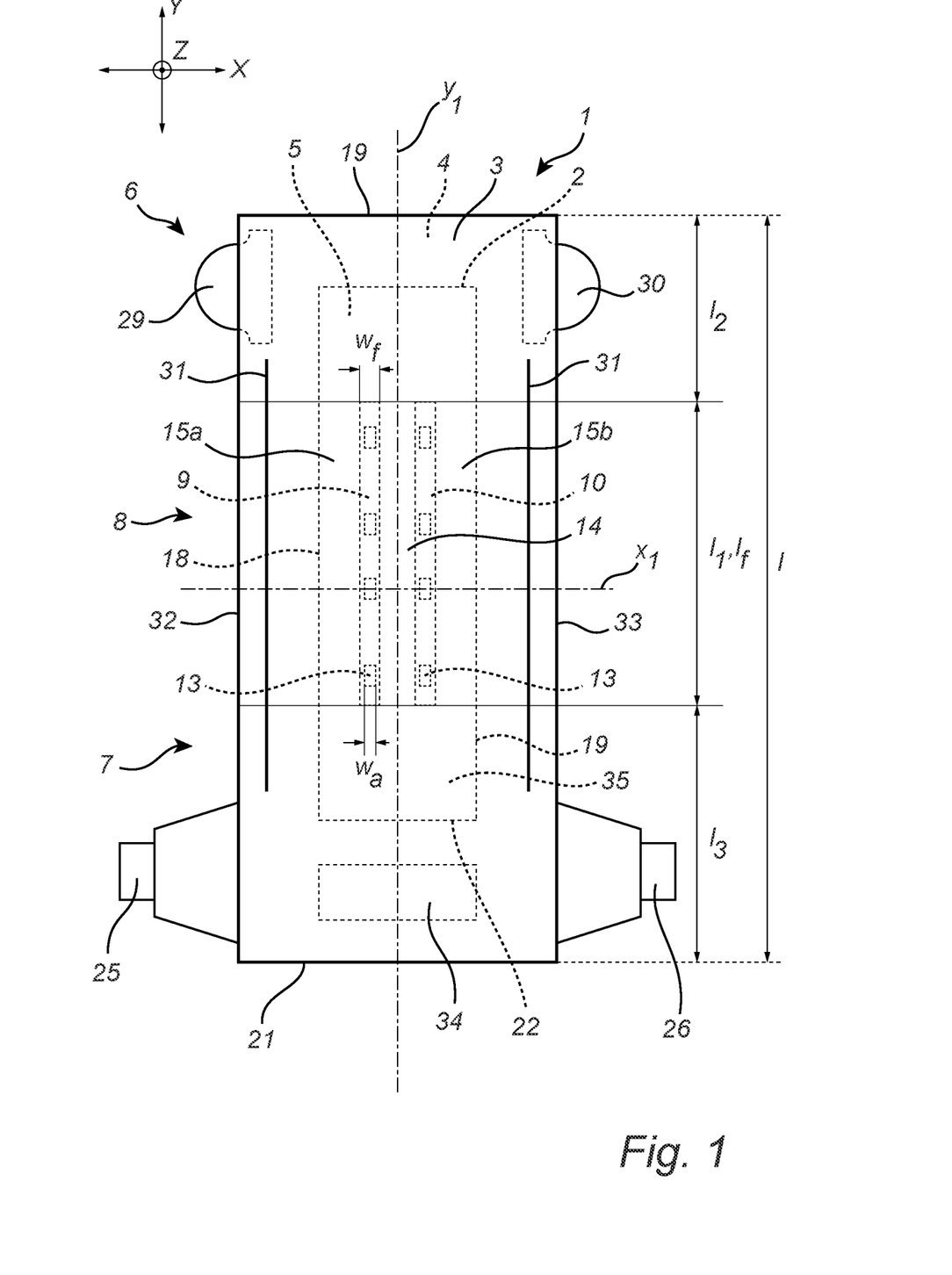
FIG. 1 shows a view from an inner surface of an absorbent article in the form of a diaper.

With initial reference to FIG. 1, there is shown an absorbent article 1 in the form of a baby diaper. The absorbent article 1 is shown in FIG. 1 in an unfolded and flat condition with all elastic elements in an extended state.

The absorbent article 1 is seen from the surface which will be facing a wearer's body when the article is being worn and comprises a liquid-permeable topsheet 3, a liquid-impermeable backsheet 4 and an absorbent core 5 which is sandwiched between the topsheet 3 and the backsheet 4. The topsheet 3 is arranged at the inner or wearer-facing surface of the absorbent article 1, whereas the backsheet 4 is arranged at the outer or garment-facing surface of the absorbent article 1.

The absorbent core shown in FIG. 1 has a rectangular design. However, as set out herein, the disclosure is not limited to rectangular cores and it is to be understood that the absorbent core may have any useful shape, such as hourglass shape T-shape, H-shape, etc., as known in the art.

The topsheet 3, the backsheet 4 and the absorbent core 5 may be constituted by any suitable materials, as will be discussed in further detail below.

As shown in FIG. 1, the absorbent article 1 has a longitudinal direction Y with a central longitudinal axis $y_1$ extending in the longitudinal direction Y and a transverse direction X with a central transverse axis $x_1$, which is perpendicular to the central longitudinal axis $y_1$. The absorbent article 1 may be defined as being divided into a front portion 6 having a length $l_2$, a rear portion 7 having a length $l_3$ and a crotch portion 8 having a length $l_1$. The front portion 6 has a front waist edge constituting a front end edge 19 of the absorbent article 1 and the rear portion 7 has a rear waist edge constituting a rear end edge 21 of the absorbent article 1. Leg edges are formed by longitudinally extending side edges 32, 33 of the absorbent article 1. The front portion 6 is the part of the absorbent article 1 which is intended to be oriented in a direction towards the belly of the wearer during use of the absorbent article 1 and the rear portion 7 is the part of the absorbent article 1 which is intended to be oriented in a direction towards the buttocks of the wearer.

The absorbent article 1 in FIG. 1 is an open-type diaper having front gripping tabs 29, 30 extending from the side edges 32, 33 at the front end edge 19 of the absorbent article 1 and rear fastener tabs 25, 26 extending from the side edges 32, 33 at the rear end edge 21 of the absorbent article 1. When applying the absorbent article 1 to a wearer, the rear fastener tabs 25, 26 are brought forward towards the wearer's belly and are attached with fastener elements, such as hook-type fastener elements onto mating fastener elements, such as loop-type fastener elements which are provided on the outer surface of the front portion 6 of the absorbent article.

It is to be understood that male fasteners, such as hook-type fasteners may instead be placed at the front of the article while female fasteners may be placed at the rear of the article. Furthermore, the fastening arrangement may differ from that shown in FIG. 1 and may be of any useful kind as known in the art. Accordingly, fastener belts, girdles, adhesive fastening systems, etc. may be used. It should also be noted that the fastening system is optional to the absorbent article 1, as the article may be designed for use as an absorbent insert, worn inside a pair of supportive pants or ordinary underpants. Such articles may be provided with fastening adhesive arranged on the outer surface of the backsheet, to allow the article to be fastened inside the pants. Furthermore, the absorbent article may be a pant-type article which is provided in a pre-assembled configuration, with closed side seams. Such articles may nevertheless be provided with a fastening system, to allow the article to be opened and reclosed.

The absorbent core 5 is sandwiched between an upper core cover layer 11 and a lower core cover layer 12, which together constitute a core cover 35 enclosing the absorbent core 5. The core cover 35 is a component of the absorbent article 1 in FIG. 1 which is provided in addition to the topsheet 3 and the backsheet 4. The absorbent core 5 has a front edge 2 and a rear edge 22.

The absorbent core 5 which is shown in FIG. 1 is formed with two longitudinally extending and generally straight absorbent material free areas 9, 10. The absorbent material free areas 9, 10 are elongated and have a main extension in the longitudinal direction Y with a length $l_f$ as measured along the respective elongated absorbent material free area 9, 10 and a width $w_f$ in the width direction X. In the absorbent article shown in FIG. 1, the length $l_f$ of the absorbent material free areas 9, 10 is equal to the length $l_1$ of the crotch portion 8. The upper core cover layer 11 and the lower core cover layer 12 are attached to each other within spaced-apart attachment zones 13 which are arranged in each of the elongated absorbent material free areas 9, 10. The attachment zones are spaced-apart in the longitudinal direction Y within the absorbent material free areas 9, 10. In the absorbent article 1 shown in FIG. 1 and the absorbent core 5 shown in FIG. 2, four attachment zones 13 are provided in each elongated absorbent material free area 9, 10. In the absorbent articles as disclosed herein, a smaller or greater number of attachment zones may be provided in each elongated absorbent material free area, such as at least 2 attachment zones and at most 12 attachment zones in each absorbent material free area.

A width $w_a$ of each attachment zone 13 may be less than the width $w_f$ of the corresponding absorbent material free area 9, 10 in which the attachment zone 13 is arranged. Thereby, a slack is formed in the core cover material between the edge of the attachment zone 13 and the edge of the absorbent material free area 9, 10 in which the attachment zone 13 is placed. Such slack may allow the attachment zones 13 to be formed in the absorbent material free areas 9, 10 without causing the absorbent material on each side of the absorbent material free areas 9, 10 to become unduly compressed at the attachment zones 13.

As set out herein, the disclosure is not limited to a core cover comprising two core cover layers. The core cover may be of one single material layer which has been wrapped around the absorbent core and sealed at a side edge of the absorbent core or along a surface of the absorbent core. Furthermore, the absorbent component may be enclosed by a continuous tubular core cover.

The upper core cover layer 11 and the lower core cover layer 12 may be attached to each other by any useful means as known in the art, for example, by thermo-mechanical bonding, such as thermo-sealing, ultrasonic bonding, an adhesive or adhesives, stitching or the like, or combinations thereof.

Figure 2:
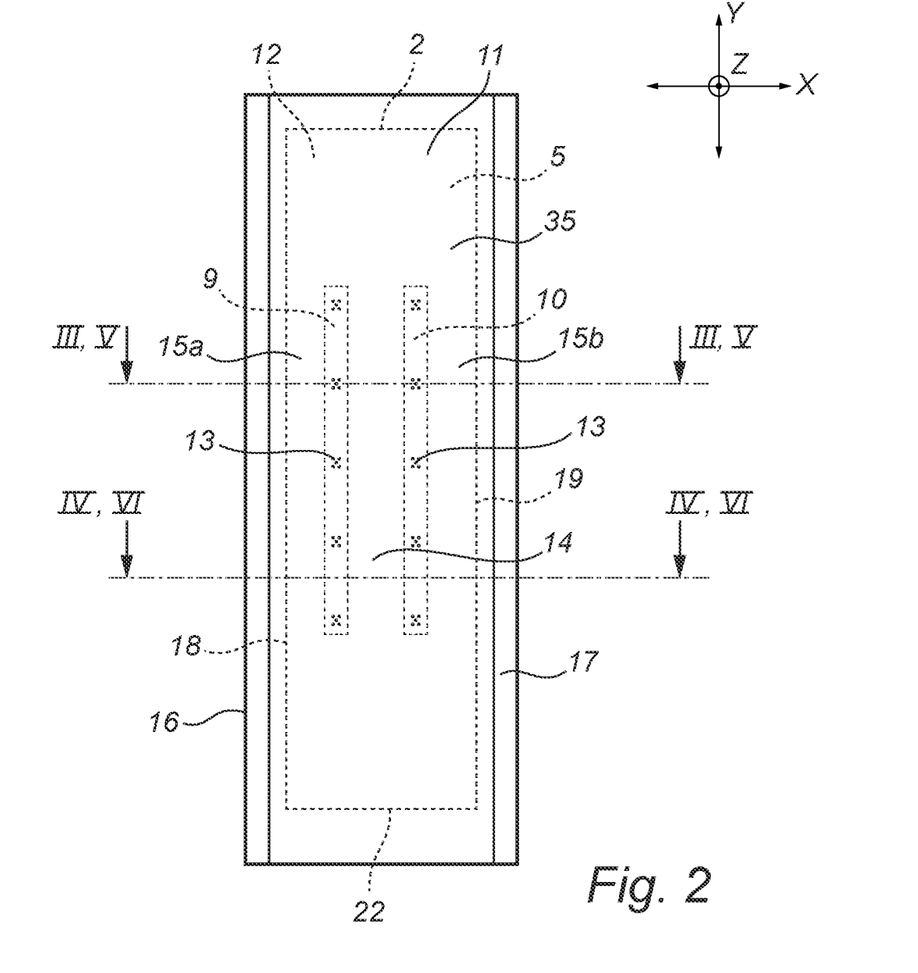
FIG. 2 shows a top view of an absorbent core enclosed in a core cover.

As shown in FIGS. 1 and 2, in the part of the absorbent core 5 in which the absorbent material free areas 9, 10 are arranged, the absorbent core 5 is divided into a central segment 14 located between the absorbent material free areas 9, 10 and two side segments 15a, 15b which are located between one of the absorbent material free areas 9, 10 and a corresponding side seam 16, 17 joining the upper core cover layer 11 to the lower core cover layer 12 along each of the side edge 18, 19 of the absorbent core 5. The side seams 16, 17 may be formed by any suitable joining technique such as ultrasonic welding, heat welding, adhesive, needling, etc. as disclosed for the attachment zones 13.

The absorbent core 5 which is shown in FIG. 2, may be used in the absorbent article as shown in FIG. 1 and has a generally rectangular shape and is provided with two generally straight absorbent material free areas 9, 10 which extend in the longitudinal direction Y. As set out herein the disclosure is not limited to a rectangular absorbent core 5 and straight absorbent material free areas 9, 10. The absorbent core 5 may have any useful shape and the absorbent material free areas may deviate from the straight shape shown in the Figs. Moreover, the absorbent core may be provided with a single absorbent free area or more than two absorbent free areas may be arranged in the absorbent core.

As disclosed herein, the length $l_c$ of the crotch portion 8 may be equal to the length of the absorbent material free areas 9, 10, i.e. the absorbent material free areas 9, 10 may be arranged only in the crotch portion 8 of the absorbent article 1. However, the absorbent material free areas 9, 10 may also extend into the front portion 6 and/or into the rear portion 7. Furthermore, one or more absorbent material free area may be arranged only in the front portion 6 and/or in the rear portion 7.

The absorbent material free areas 9, 10 of the absorbent core 5 which is shown in FIG. 2 has five attachment zones 13 arranged in each of the absorbent material free areas 9, 10.

The attachment zones 13 are shown to have a rectangular shape and may have a length/width ratio of 1/1 or a length/width ratio within the range of from 0.8/1 to 4/1, such as within the range of from 0.9/1 to 3/1, within the range of from 1/1 to 2/1 or within the range of from 1/1 to 1.5/1.

Figure 7:
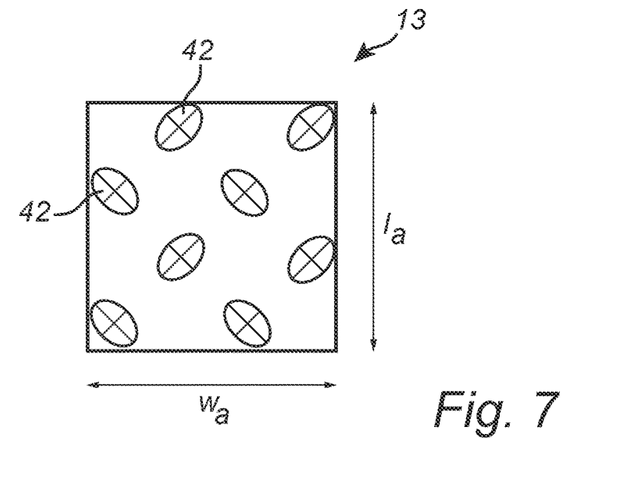
FIG. 7 shows an attachment zone as disclosed herein.

As illustrated in FIG. 7, each attachment zone 13 contains of a cluster of eight individual weld bonds 42. The number of individual weld bonds 42 in the attachment zones 13 may be different from that shown in FIG. 7, such as a singular individual weld bond or a cluster of 2 to 30 individual weld bonds, such as a cluster of 3 to 20 individual weld bonds or a cluster of 5 to 10 individual weld bonds. The individual weld bonds in the cluster of individual weld bonds may have a different shape from the oval shape shown in FIG. 7, such as a rectangular shape, a circular shape, a triangular shape, etc., as set out herein. Furthermore, the individual weld bonds may have a distribution pattern within the attachment zone 13 which differs from the staggered distribution pattern shown in FIG. 7.

Figure 3:
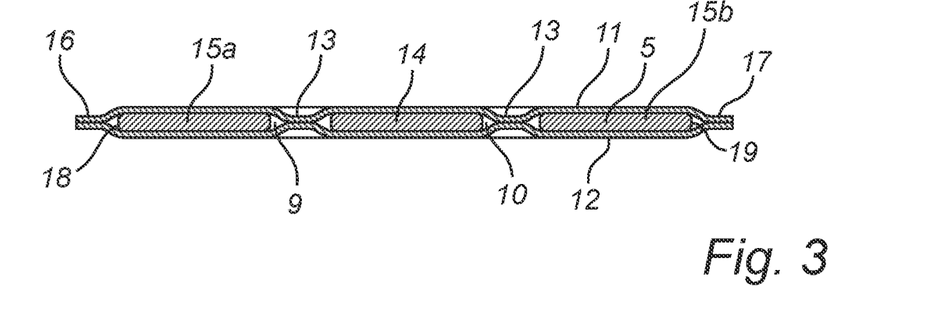
FIG. 3 shows a cross section through the absorbent core in FIG. 2, taken along the line when the absorbent core is in a dry state.
Figure 4:
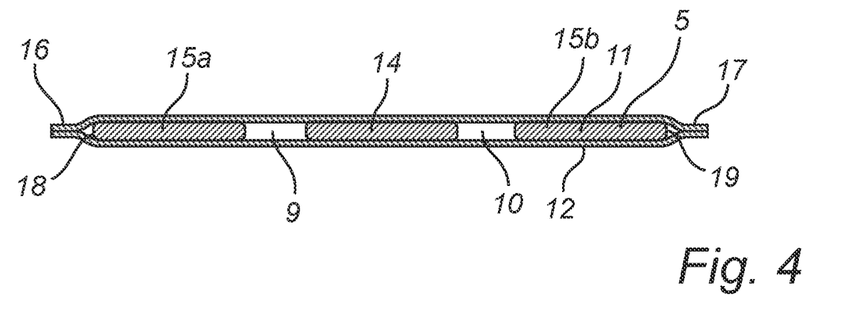
FIG. 4 shows a cross section through the absorbent core in FIG. 2, taken along the line IV-IV when the absorbent core is in a dry state.

FIGS. 3 and 4 are cross sections through the absorbent core 5 in FIG. 2. The cross sections are taken along the lines and IV-IV of the absorbent core while in a dry condition before the absorbent core 5 has absorbed any liquid. FIG. 3 illustrate how the upper core cover layer 11 is joined to the lower core cover layer in the attachment zones 13 in the absorbent material free areas 9, 10. In FIG. 4 the absorbent material free areas 9, 10 are clearly visible between the central segment 14 of the absorbent core 5 and the side segments 15a, 15b of the absorbent core 5.

Figure 5:
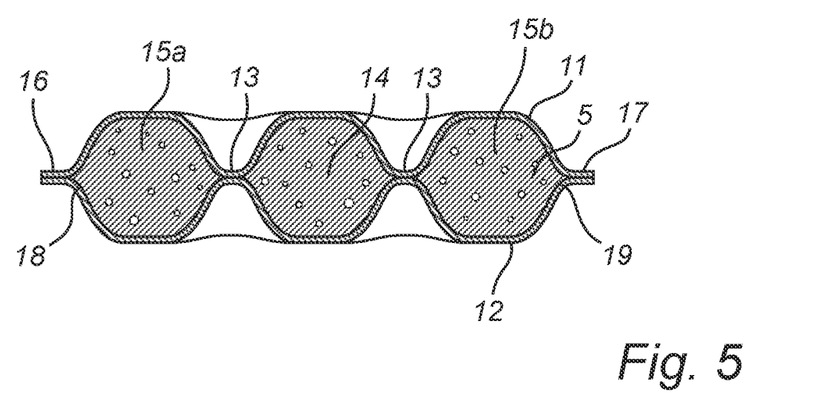
FIG. 5 shows a cross section through the absorbent core in FIG. 2, taken along the line V-V when the absorbent core is in a wet state.
Figure 6:
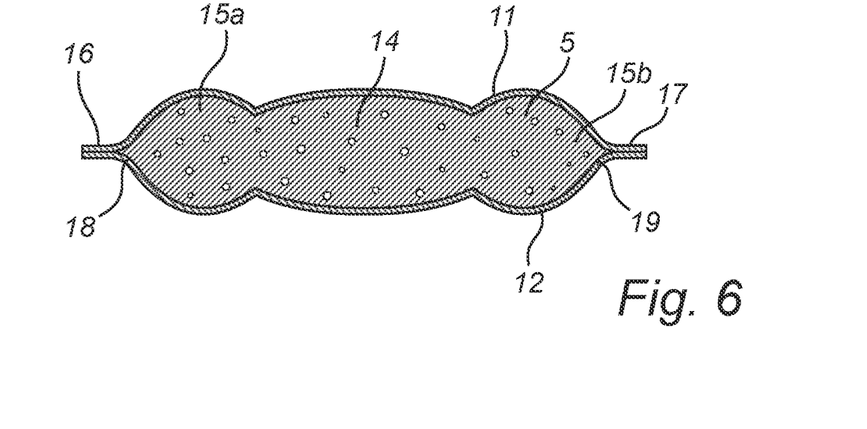
FIG. 6 shows a cross section through the absorbent core in FIG. 2, taken along the line VI-VI when the absorbent core is in a wet state.

The cross sections in FIGS. 5 and 6 correspond to the cross sections shown in FIGS. 3 and 4. FIGS. 5 and 6 show how the absorbent core appears at the attachment zones 13 and in the attachment zone free parts of the absorbent material free areas 9, 10 after the absorbent core 5 has absorbed liquid and the absorbent material has swollen and expanded into the absorbent material free areas 9, 10. The attachment zones 13 in which the upper core cover layer and the lower core cover layer are connected with each other constitute restriction means which limit swelling in a thickness direction Z of the absorbent article by prohibiting the upper core cover layer 11 and the lower core cover 12 layer from freely moving away from each other. As can be seen in FIG. 6, the absorbent material in the central segment 14 as well as in the side segments 15a, 15b of the absorbent core 5 has expanded into the absorbent material free areas 9, 10 which are filled with swollen absorbent material to the extent that the absorbent material free areas 9, 10 are virtually obliterated.

It can also be seen from FIGS. 3 to 6 that the slack provided between the absorbent core 13 and the core cover layers 11, 12 at the attachment zones 13 and along the side edges 18, 19 of the absorbent core 5 is filled with swollen absorbent material when the absorbent core is in a wet state, as it will appear when it is being used and has absorbed a full amount of body fluid.

The absorbent article 1 shown in FIG. 1 further comprises leg elastic elements 31 extending along each longitudinal side edge 32, 33 of the absorbent article 1. The leg elastic elements 31 have a greater length in the longitudinal direction Y than the length $l_f$ of the absorbent material free areas 9, 10. Accordingly, the leg elastic elements 31 have an extension not only in the crotch portion 8 but also in a part of the front portion 6 and the rear portion 7. The leg elastic elements 31 of the absorbent article 1 as shown in FIG. 1, have a greater extension in the rear portion 7 than in the front portion 6. The configuration and extension of the leg elastic elements 31 as shown in FIG. 1 are non-essential features of the absorbent articles 1 as disclosed herein.

The absorbent article 1 further has a waist elastic element 34 located in the rear portion 7 close to the rear end edge 21 of the absorbent article 1. It is to be understood that also the front end edge 19 may be provided with waist elastic, if desired.

The leg elastic elements and the waist elastic element are optional features of an absorbent article as disclosed herein.

Various types of materials may be used for the different components of the absorbent article 1. The topsheet 3 which is arranged to face the wearer of the absorbent article 1 when the article is being worn may comprise or consist of any suitable topsheet material as known in the art. Useful topsheets are fluid permeable materials such as nonwoven fabric, perforated plastic film, knitted, woven or cast mesh, or open-cell foam material. The topsheet may be made from thermoplastic material, such as thermoplastic synthetic fibers, thermoplastic film or netting. The topsheet 3 is preferably sufficiently liquid-permeable to allow discharged body fluid to rapidly penetrate through the thickness of the topsheet 3. Also, the topsheet 3 may suitably be manufactured from a material which is compliant and soft-feeling to the skin of the wearer. The topsheet 3 may consist of a single layer or may comprise a plurality of layers, for example, two or more layers. The layers may be made of the same material, or some or all of the layers may be made of different materials. Topsheet materials commonly have a basis weight in the range of from 8-40 $g/m^2$.

The backsheet 4 is preferably resistant to liquid penetration and may be constituted by a liquid-impermeable layer such as a polymeric film, for example a film of polyethylene or polypropylene. The backsheet 4 may be breathable. The materials which may be used for the backsheet 4 include thin and flexible fluid impermeable plastic films, or fluid impermeable nonwoven materials, fluid impermeable foams and fluid impermeable laminates. The backsheet 4 may be formed by a single layer, of may be a multi-layered structure, i.e. a laminate, wherein at least one layer is fluid impermeable. Furthermore, the backsheet 4 may be elastic in any direction. Furthermore, the backsheet 4 may have a laminate structure comprising a liquid barrier layer and a nonwoven layer arranged on an outer surface of the absorbent article 1, i.e. on a surface of the absorbent article which will be facing away from the wearer during use of the article.

The nonwoven layer may comprise or consist of thermoplastic polymer fibers or filaments. The nonwoven layer may be formed by any of a variety of different processes as known in the art, such as spunbonding, airlaying, meltblowing or bonded carded web formation processes. The nonwoven layer may be a layer comprising sublayers or lamina such as an SMS nonwoven material (spunbond/meltblown/spunbond), an SMMS nonwoven material (spunbond/meltblown/meltblown/spunbond) or an SS nonwoven material (spunbond/spunbond). The fibres in the nonwoven layer may be polypropylene or bicomponent fibers of polypropylene and polyethylene, or of a combination of such materials. The nonwoven layer may have a basis weight in the range of 5-40 g/m$^2$.

Regarding the choice of materials for the various layers in the absorbent article, the materials may be chosen with consideration for the bonding processes used when forming seals and bonds between components of the absorbent article, such as the bonds in the absorbent material free areas and the side seams. For example, if ultrasonic welding is chosen for joining the upper and lower core cover layers, the materials for the core cover may contain a sufficient amount of thermoplastic material to allow secure and durable bonds to be formed.

The absorbent article 1 includes the absorbent core 5 and may include further absorbent components and absorption control components such as components which provide liquid acquisition and liquid distribution. The absorbent core is disposed between the topsheet 3 and the backsheet 4 to absorb liquid, such as urine or other bodily fluids, which have passed through the topsheet 3. The absorbent core 5 may be a single-layer structure or may be a layered structure, within all or only part of the core. The absorbent core 5 preferably comprises superabsorbent material. Such superabsorbent material is well known in the field of absorbent articles and is constituted by water-swellable and water-insoluble material which is capable of absorbing large quantities of fluid upon formation of a hydrogel. The absorbent core may contain superabsorbent material in the form of fibers or particles of absorbent polymer material. For example, the superabsorbent material may be surface crosslinked, partially neutralized polyacrylates. The superabsorbent material, e.g., the superabsorbent fibers or particles, may be mixed with other absorbent or liquid uptake material or materials, such as cellulose fluff pulp. The amount of superabsorbent material and pulp in the absorbent core 5 may be from 0 to 70 weight % pulp fibers and from 30 to 100 weight % superabsorbent material.

The absorbent core 5 may further comprise components for improving properties of the absorbent core 5, such as core integrity and strength. For example, the absorbent core 5 may comprise a binder or binders, such as binder fibers. Resilient fibers, chemically stiffened fibers, etc. may be present in the absorbent component to counteract wet-collapse of cellulosic fibers. Such fibers may also be useful in retaining a fluid transporting capillary network in the absorbent component so that absorbent fluid may be distributed in the absorbent component and be absorbed by superabsorbent material also in parts of the absorbent component outside the initial wetting area of the absorbent article.

The core cover 35 may be formed by a separate upper core cover layer 11 and a separate lower core cover layer 12. However, the disclosure is not limited to a core cover comprising two separate core cover layers. The core cover layers 11, 12 may also be formed from one single material layer which is folded to create the upper core cover layer 11 and the lower core cover layer 12. The absorbent core 5 may be enclosed by a core cover material which is folded in two and sealed at least in the longitudinal direction and optionally also in the transverse direction. Furthermore, the absorbent core may be enclosed by a continuous, tubular core cover sheet. The basis weight of the core cover material may be in the interval of from 5 g/m$^2$ to 20 g/m$^2$. The core cover material may be made of thermoplastic polymer material. The core cover material may be nonwoven material. The nonwoven material may be made of thermoplastic polymer material fibers or filaments. The nonwoven layer may be formed by any of a variety of different processes, such as spunbonding, airlaying, meltblowing or bonded carded web formation processes. The nonwoven layer may be a layer comprising sublayers or lamina such as an SMS nonwoven material (spunbond/meltblown/spunbond), an SMMS nonwoven material (spunbond/meltblown/meltblown/spunbond) or an SS nonwoven material (spunbond/spunbond). The fibres in the nonwoven layer may be polypropylene or bicomponent fibers of polypropylene and polyethylene, or of a combination of such materials.

Furthermore, the absorbent article 1 may comprise construction adhesive for attaching components to each other. Such adhesive is not shown in the drawings.

One or more additional layers may be provided in the absorbent article 1. For example, an acquisition layer may be arranged between the absorbent core 5 and the topsheet 3. Such an additional layer may for example be in the form of an airlaid layer, a spunlace layer, a high-loft fiber material, an open-cell or perforated foam or any other type of material layer or combination of layers which may be used in an absorbent article to act as a liquid handling layer providing functions such as liquid acquisition, liquid absorption and liquid distribution. A liquid acquisition layer is adapted to quickly receive and temporarily store discharged liquid before the liquid can be absorbed by the absorbent component. Such acquisition layer may be composed of for example airlaid nonwoven, spunlace nonwoven, high loft nonwoven or foam materials. An airlaid nonwoven may be produced wood pulp fluff fibers which are dispersed and suspended in a fast-moving air stream and condensed onto a moving screen by means of pressure and vacuum.

With reference again to FIG. 1, each absorbent material free area 9, 10 may have a length which corresponds to the longitudinal extension of the crotch portion 8. Each one of the absorbent material free areas 9, 10 may have a length $l_1$ which is between 5-50%, such as 10-50%, such as 28-38%, of the total length l of the absorbent article 1. Furthermore, each absorbent material free area 9, 10 may have a length $l_1$ which is between 10-60%, such as between 20-60%, such as between 30-50%, of the length of the absorbent core 5.

A further parameter which may be varied is the positioning of the absorbent material free areas 9, 10 in the longitudinal direction of the absorbent article 1.

The position of the absorbent material free areas 9, 10 in the longitudinal direction of the absorbent article 1 may be chosen so that each absorbent material free area 9, 10 terminates at a distance from the front end edge 19 of the article 1 which is between 15-40%, such as between 22-25%, of the total length l of the article 1.

Furthermore, the topsheet may comprise at least one additive material such as a skin care composition. The additive may be located on parts of the topsheet which are disposed along the longitudinal side edges 32, 33 of the absorbent article 1 and/or along the longitudinal side edges 18, 19 of the absorbent core 5. An advantage with such placement of the additive material, is that as the parts of the absorbent article 1 which are arranged along the side edges normally will be closer to the body of the wearer of the absorbent article 1 than a longitudinally central part of the absorbent article 1, the skin care benefits of the additive may be obtained without the additive interfering with fluid acquisition through the topsheet 3 in the central part of the absorbent article 1.

The absorbent article 1 may further be provided with elasticated raised barrier cuffs arranged along the longitudinal side edges 32, 33 of the absorbent article 1.

Figure 8:
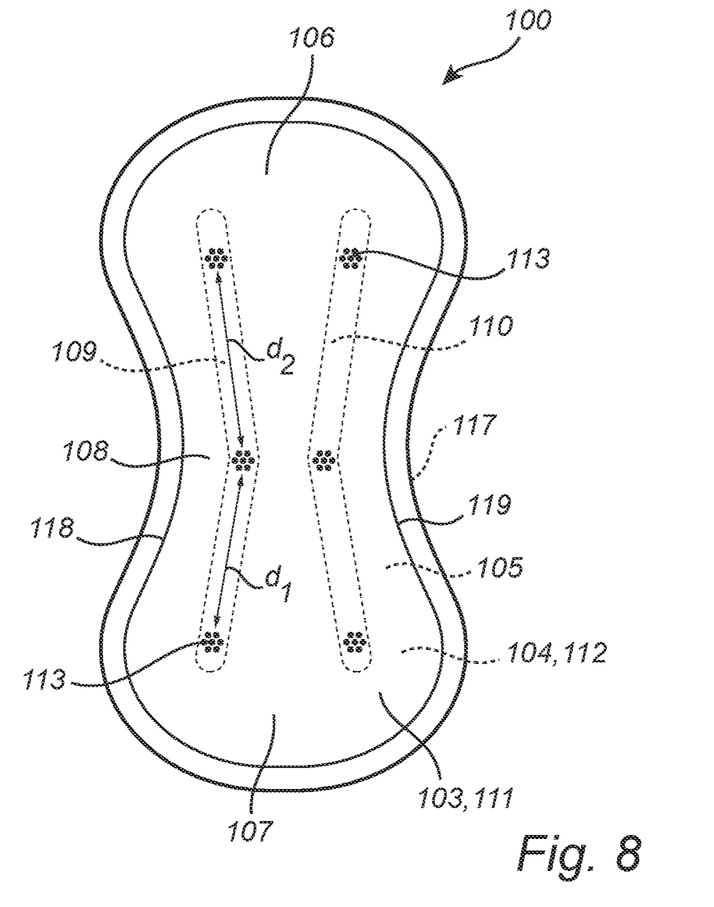
FIG. 8 shows a view from an inner surface of an absorbent article in the form of an incontinence protector.

A further example of an absorbent article 100 having absorbent material free areas 109, 110 arranged between a liquid-permeable topsheet 103 constituting an upper core cover layer 111 and a liquid-impermeable backsheet 104 constituting a lower core cover layer 112 is shown in FIG. 8. The topsheet 103 and the backsheet 104 are attached to each other in an edge seal 117 extending along the full periphery of the absorbent article 100. The absorbent article 100 in FIG. 8 may be an incontinence protector or a sanitary napkin, i.e, an article which is intended to be worn inside a pair of ordinary underpants, or support pants. Such articles may be provided with fastening adhesive, on the outer surface of the backsheet 104 for fastening the absorbent article 100 inside of the pants. The absorbent core 105 is sandwiched between the topsheet 103 and the backsheet 104. No separate core cover is provided in the absorbent article shown in FIG. 8. FIG. 8 further illustrates that the absorbent material free areas 109, 110 in the articles as disclosed herein may have a shape deviating from the straight shape shown in FIGS. 1 and 2. In the absorbent article 100 shown in FIG. 8, the absorbent material free areas 109, 110 has a shape which follows the hour-glass shape of the absorbent core 105.

The absorbent article 100 has a front portion 106, a rear portion 107 and a crotch portion 108.

FIG. 8 also illustrates that the attachment zones 113 in the absorbent material free areas 109, 110 may be arranged with different spacing between the attachment zones 113. Accordingly, the distance $d_1$ between the two rear-most attachment zones 113 in each absorbent material free area 109, 110 is smaller than the distance $d_2$ between the two forward attachment zones 113 in each absorbent material free area 109, 110, as measured from edge-to-edge of the attachment zones 113 along the respective absorbent material free area 109, 110.

The invention claimed is:

1. An absorbent article comprising an absorbent core, the absorbent core comprising absorbent material, the absorbent core being sandwiched between a liquid-permeable upper core cover layer and a lower core cover layer, the article having a longitudinal direction (Y) and a transverse direction (X) perpendicular to the longitudinal direction, the absorbent core having a first side edge and a second side edge, the first side edge and the second side edge of the absorbent core each extending in the longitudinal direction (Y), the upper core cover layer and the lower core cover layer being connected along the side edges of the absorbent core, the absorbent core having one or more elongated areas arranged therein, each elongated area being an absorbent material free area and having a main extension in the longitudinal direction (Y) with a length ($l_f$) as measured along the elongated area and a width ($w_f$) in the transverse direction (X), wherein the upper core cover layer and the lower core cover layer in each of the one or more elongated absorbent material free areas are attached to each other within at least 2 attachment zones and at most 12 attachment zones, the attachment zones being spaced-apart in the longitudinal direction (Y) within each of the one or more absorbent material free areas with a width ($w_a$) in the transverse direction (X), the width ($w_a$) of the attachment zone being smaller than the width ($w_f$) of the absorbent material free area, wherein an absorbent material free area exists on each side of each of the attachment zones in the lateral direction between the upper core cover layer and the lower core cover layer in a dry condition.

2. An absorbent article according to claim 1, wherein both the upper core cover layer and the lower core cover layer are liquid-permeable cover layers.

3. An absorbent article according to claim 1, wherein the upper core cover layer and the lower core cover layer together form a core cover, and wherein the upper core cover layer and the lower core cover layer are formed from a single continuous material layer or from two separate material layers.

4. An absorbent article according to claim 1 wherein the absorbent article in addition to the upper core cover layer and the lower core cover layer comprises a liquid permeable topsheet and a liquid barrier layer, the absorbent core being arranged between the liquid permeable topsheet and the liquid barrier layer with the upper core cover layer facing the liquid permeable topsheet and the lower core cover layer facing the liquid barrier layer.

5. An absorbent article according to claim 1, wherein the absorbent core comprises super-absorbent material.

6. An absorbent article according to claim 5, wherein the absorbent core comprises from 30% by weight to 100% by weight of superabsorbent material.

7. An absorbent article according to claim 1, wherein the attachment zones have a length/width ratio within the range of from 0.8/1 to 4/1.

8. An absorbent article according to claim 7, wherein each attachment zone consists of a single weld bond or of a cluster of 2 to 200 individual weld bonds.

9. An absorbent article according to claim 7, wherein the attachment zones have a length/width ratio within the range of from 1/1 to 2/1.

10. An absorbent article according to claim 7, wherein the attachment zones have a length/width ratio within the range of from 1/1 to 1.5/1.

11. An absorbent article according to claim 7, wherein the attachment zones have a length/width ratio within the range of from 0.9/1 to 3/1.

12. An absorbent article according to claim 1, wherein the attachment zones are formed by heat welding or ultrasonic welding.

13. An absorbent article according to claim 1, wherein the length of each of the one or more elongated absorbent free areas is in the range of from 50 mm to 500 mm.

14. An absorbent article according to claim 1, wherein each attachment zone has a surface area in the range of from 3 mm$^2$ to 400 mm$^2$.

15. An absorbent article according to claim 1, wherein the absorbent core comprises more than one elongated absorbent material free area.

16. An absorbent article according to claim 1, wherein the absorbent core comprises two or more parts having different absorption capacity, each of the at least one or more elongated areas being arranged in the one or more parts having different absorption capacity, wherein the attachment zones in each of the one or more elongated areas are more closely spaced apart within a part of the absorbent core having lower absorption capacity than in a part of the absorbent core having higher absorption capacity.

17. An absorbent article according to claim 1, wherein the absorbent article is a baby diaper.

18. An absorbent article according to claim 1, wherein the attachment zones are permanent attachments.

19. An absorbent article comprising an absorbent core, the absorbent core comprising absorbent material, the absorbent core being sandwiched between a liquid-permeable upper core cover layer and a lower core cover layer, the article having a longitudinal direction (Y) and a transverse direction (X) perpendicular to the longitudinal direction, the absorbent core having a first side edge and a second side edge, the first side edge and the second side edge of the absorbent core each extending in the longitudinal direction (Y), the upper core cover layer and the lower core cover layer being connected along the side edges of the absorbent core, the absorbent core having one or more elongated areas arranged therein, each elongated area being an absorbent material free area and having a main extension in the longitudinal direction (Y) with a length ($l_f$) as measured along the elongated area and a width ($w_f$) in the transverse direction (X), wherein the upper core cover layer and the lower core cover layer in each of the one or more elongated absorbent material free areas are attached to each other within at least 2 attachment zones and at most 12 attachment zones, the attachment zones being spaced-apart in the longitudinal direction (Y) within each of the one or more absorbent material free areas, wherein the attachment zones are spaced apart in the longitudinal direction with a closest distance in the longitudinal direction between neighboring attachment zones of from 15 millimeters to 119 millimeters.

20. An absorbent article according to claim 19, wherein the attachment zones are spaced apart in the longitudinal direction with a closest distance in the longitudinal direction between neighboring attachment zones of from 35 millimeters to 50 millimeters.

21. An absorbent article according to claim 19, wherein each of the one or more absorbent material free areas has a width ($w_a$) in the transverse direction (X), the width ($w_a$) of the attachment zone being smaller than the width ($w_f$) of the absorbent material free area.

* * * * *